United States Patent [19]
Hung

[11] Patent Number: 5,902,582
[45] Date of Patent: *May 11, 1999

[54] USE OF TFPI INHIBITOR FOR TREATMENT OF CANCER

[75] Inventor: David T. Hung, San Francisco, Calif.

[73] Assignee: Chiron Corporation, Emeryville, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/699,897

[22] Filed: Aug. 15, 1996

Related U.S. Application Data

[60] Provisional application No. 60/003,194, Sep. 5, 1995.
[51] Int. Cl.$^6$ .................................................. A61K 38/00
[52] U.S. Cl. ........................................... 424/130.1; 514/12
[58] Field of Search .................... 524/12–19; 424/158.1, 424/130.1; 530/388.25, 389.3

[56] References Cited

U.S. PATENT DOCUMENTS 5,147,638   9/1992   Esmon et al. .

FOREIGN PATENT DOCUMENTS

WO 94/02172   2/1994   WIPO .

OTHER PUBLICATIONS

Dillman, Annals of Internal Medicine vol. 111 p. 592, 1989.
Osband et al, Immunology TodaY vol. 11 p. 193, 1990.
Scholm, Molecular Foundations of Oncology, Broder, ed. Chapter 6, 1991.
Johnson et al. Cancer Treatment Reviews vol. 2 p. 1, 1975.
Ameri, et al, Blood 79(12):3219–26 (1992).
Beretz et al, Bioheology 27(3–4): 455–60 (1990).
Denekamp, British J. Radiology 66(783): 181–196 (1993).
Herbert et al, Thrombosis Research 71(6): 487–93 (1993).
Ito et al, Febs Letters 269(1): 93–5 (1990).
Lindahl et al, Cancer 70(8): 2067–72 (1992).
Lindahl et al, Thrombosis Research 64(2): 155–68 (1991).
Lindhout et al, Blood 79(11): 2909–16 (1992).
Miyagi et al, J. Biochem. 116(5): 939–42 (1994).
Salgadao et al. Haemostasis, 24(2): 132–8 (1994).
Sandset et al, Blood 78(6): 1496–502 (1991).
Taylor, Progress in Clinical and Biological Research, 388:175–94 (1994).
Tijburg, J. Biol. Chem. 266(18) 12067–74 (1991).
Creasey et al., "Tissue Factor Pathway Inhibitor Reduces Mortality from *Escherichia coli* Septic Shock" *J. Clin. Invest.* 91(6):2850–2860, Jun. 1993.
Werling et al., "Distribution of Tissue Factor Pathway Inhibitor in Normal and Malignant Human Tissues" *Thrombosis and Haemostasis* 69(4):366–369, Apr., 1993.

*Primary Examiner*—Sheela Huff
*Attorney, Agent, or Firm*—Robins and Associates; Robert P. Blackburn

[57] ABSTRACT

The invention provides for the inhibition of the activity of TFPI to prevent TFPI from countering the procoagulant activities associated with many tumors. Inhibition of TFPI activity by the method of the invention facilitates the propensity toward thrombosis in malignancies and therefore promotes tumor cell death. The method of the invention also includes, in addition to the administration of an inhibitor of TFPI, co-administration of an agent capable of inducing or augmenting in the targeted tumor the release or induction of factors that initiate or enhance clotting, such as TF and Factors VIIa and Xa.

17 Claims, No Drawings

USE OF TFPI INHIBITOR FOR TREATMENT OF CANCER

CROSS-REFERENCE TO RELATED APPLICATION

This application is related to provisional patent application Ser. No. 60/003,194, filed Sep. 5, 1995, from which priority is claimed under 35 U.S.C. §119(e)(1) and which is incorporated herein by reference in its entirety.

FIELD OF THE INVENTION

This invention relates to a method of induction of tumor cell death and, hence, a method of treatment of cancer, by administering to an individual in need of treatment a therapeutically effective amount of an inhibitor of tissue factor pathway inhibitor ("TFPI").

BACKGROUND OF THE INVENTION

Antibody to Protein C has been found to act in conjunction with tumor necrosis factor ("TNF") to cause tumor cell death, as described in U.S. Pat. No. 5,147,638. In contrast, treatment with TNF alone or antibody to Protein C alone is markedly less effective in the treatment of cancer. A possible explanation for the increased efficacy of combined antibody to Protein C and TNF may be that TNF induces or augments the expression of tissue factor ("TF") by tumor cells or non-tumor cells such as infiltrating white blood cells or endothelial cells associated with the tumor vasculature, or induces necrosis of the tumor cells and, thus, the release of TF from the dying cells. The TF expressed or released then may initiate clotting within the tumor associated vasculature.

Protein C is an endogenous plasma protein that normally acts as a systemic anticoagulant by cleaving clotting factors, such as Factor VIII:C and Factor V. Treatment with antibody to Protein C inhibits the anti-coagulant activity of Protein C. Thus, in conjunction with agents that induce or augment tumor TF expression or release, anti-Protein C antibody may initiate or facilitate clotting within the tumor associated vasculature, compromising the blood supply to the tumor, leading ultimately to tumor cell death. Administration of antibodies to Protein C, however, may be problematic because of the likelihood of systemic thrombosis as a serious side effect. TFPI is an endogenous, systemically circulating plasma protein which functions as a physiological anticoagulant by inhibiting TF/Factor VIIa complexes and preventing them from activating the extrinsic pathway of coagulation. Cellular TF expression occurs generally only under pathological conditions, including but not limited to, for example, vasculature disruption, wounds, malignancy, sepsis, and other conditions. Regulation of TFPI, therefore, may be an important mechanism for regulating the amount of TF-mediated coagulation in these pathological conditions.

TFPI also acts to inhibit what is known in the art as "the common pathway of coagulation" by inhibiting Factor Xa. TFPI is therefore also probably important in regulating the amount of Xa-mediated coagulation in situations in which Xa formation might occur independently of TF/Factor VIIa activation, for example, as in the case of certain mucinous adenocarcinomas that possess proteins capable of directly activating Factor X to Factor Xa.

With regard to a treatment for cancer, therefore, it would be desirable if thrombosis can be induced locally or can be targeted to a particular region, for example, specifically to tumor tissues so as to avoid generalized thrombosis.

SUMMARY OF THE INVENTION

It is an object of the present invention to promote tumor autoinfarction and to promote tumor cell death by inhibition of the activity of TFPI. In accordance with this object, therefore, the present invention is directed to the use of an inhibitor of TFPI to induce tumor cell death. The invention further provides induction or augmentation of TF expression or release from the tumor or from other non-tumor cells associated with the tumor, including infiltrating white blood cells and endothelial cells in the tumor vasculature. TF expression or release can be induced or augmented by using, for example, cytokines, endotoxin, cryotherapy, hyperthermia, radiation, chemotherapeutic agents or immunotherapeutic agents. The method of the invention, hence is applicable to the treatment of any number of cancers of any origin, including but not limited to, for example, breast, prostate, lung, colon, gastric, pancreatic, ovarian, kidney, or liver carcinomas, melanomas, lymphomas, sarcomas, and particularly pancreatic, gastric, hepatic, colon, breast, ovarian, renal, lung, prostatic, and unknown site of origin primary adenocarcinomas.

DETAILED DESCRIPTION OF THE PREFERRED EMBODIMENTS

The invention described herein draws on previously published work and pending patent applications. By way of example, such work consists of scientific papers, patents or pending patent applications. All published work, including patents, and patent applications cited herein are hereby incorporated by reference.

The invention described herein is directed to use of an inhibitor of TFPI for the treatment of cancer.

The present invention provides for the inhibition of the activity of TFPI to prevent TFPI from countering the procoagulant activities associated with many tumors. Such inhibition of TFPI activity allows the induction or progression of autoinfarction of the tumor by promoting thrombosis in the tumor-associated vasculature and reducing the blood supply to the tumor. Inhibition of TFPI activity or removal of TFPI by employing the method of the invention facilitates or augments the propensity toward thrombosis in malignancies and therefore tumor cell death.

In another embodiment of the present invention, the method of the invention also includes, in addition to the administration of an inhibitor of TFPI, co-administration of an agent capable of inducing or augmenting in the targeted tumor the release or induction of factors that initiate or enhance clotting, such as TF and Factors VIIa and Xa. The targeted tumor herein includes not only the tumor cells, but also white blood cells that infiltrate the tumor, such as macrophages, lymphocytes, etc., as well as endothelial cells in the tumor vasculature. Although the invention is not limited to any theories of action of the elements of the invention, such a co-administered agent further augments the procoagulant activities of tumors. The co-administered agents include, for example, endotoxin, IL-1, IL-6, and TNF or any of a number of cytokines that are known to induce or augment the expression or release of TF or the production of TNF, as described in U.S. Pat. No. 5,147,638. It is believed that the necrotic action of certain cytokines, particularly TNF, in coordination with the TNF-induced upregulation of TF, as described in Ameri et al., *Blood,* 1992, 79(12): 3219–26, in further conjunction with the thrombic effects resulting from the introduction of a TFPI inhibitor can induce massive and tumor-localized cell death and subsequent shrinking of the tumor. Other means by which TF release or TF expression from tumors may be augmented include treatment with endotoxin, cryotherapy, hyperthermia, radiation, and chemo-, or immuno- therapies.

The invention can be better understood in light of the following definitions incorporated herein.

Definitions

A "pharmaceutically acceptable carrier" as used herein refers to one or more pharmaceutically acceptable carriers including water, saline, glycerol, or ethanol. Additionally, auxiliary substances, such as wetting or emulsifying agents, pH buffering substances, and the like, may be present. Pharmaceutically acceptable carriers are compounds and compositions that may be administered to the patient without undue toxicity. Exemplary pharmaceutically acceptable carriers can include salts, for example, mineral acid salts such as hydrochlorides, hydrobromides, phosphates, sulfates, and the like; and the salts of organic acids such as acetates, propionates, malonates, benzoates, and the like. Suitable carriers are typically large, slowly metabolized macromolecules that can be a protein, a polysaccharide, a polylactic acid, a polyglycolic acid, a polymeric amino acid, amino acid copolymers or an inactive virus particle. Such carriers are well known to those of ordinary skill in the art. A thorough discussion of pharmaceutically acceptable excipients is found in REMINGTON'S PHARMACEUTICAL SCIENCES (Mack Pub. Co., N.J. 1991.)

"Therapeutically effective amount" as used herein refers to that amount that is effective for production of a desired result which, in the case of this invention includes tumor cell death or tumor regression. The amount of inhibitor of TFPI or any adjunctive therapies including but not limited to radiation, or chemo- or immuno- therapeutic agent necessary for therapeutic effectiveness varies depending upon the health and physical condition of the individual to be treated, analyzing the risk factors peculiar to the patient, the size and growth rate of the tumors in the patient, the type and location of the tumors, the rate of progression of the disease, the responsiveness of the tumors to the dose of treatment or pattern of administration, the formulation, the attending physician's assessment of the medical situation, and other relevant factors. In the case of the administration of an inhibitor of TFPI, a therapeutically effective amount will depend on the potency of the inhibitor as well. It is expected that the amount considered therapeutically effective will fall in a relatively broad range that can be determined through routine trials.

"Co-administration" as used herein means administration of an inhibitor of TFPI according to the method of the invention in combination with a second therapeutic agent. By the method of the invention, the second therapeutic agent is an agent as described above that is capable of inducing or increasing tissue factor expression in the targeted tumor or an agent that can cause release of tissue factor from the targeted tumor. Such co-administered agents could include, for example, endotoxin, IL-1, IL-6, TNF or any of a number of cytokines that are known to induce TNF expression or release. Co-administration may be simultaneous, for example, by administering a mixture of the therapeutic agents, or may be accomplished by administration of the agents separately, such as within a short time period. Co-administration also includes successive administration of an inhibitor of TFPI and one or more of the above-described second therapeutic agents. The second therapeutic agent or agents may also be administered before or after the inhibitor of TFPI. Dosage treatment may be a single dose schedule or a multiple dose schedule.

The phrase "inducing or augmenting tissue factor expression or release" as used herein refers to use of methodology known to induce or augment tissue factor expression, or known to cause release of tissue factor from cells. Some methods known to induce or augment localized increase in TF expression or release include but are not limited to agents known to induce necrosis of the tumor tissue. These agents include but are not limited to radiation, or administration of a chemo- or immunogenic agent. Cryotherapy, such as applied to cervical tumors, and hyperthermia such as applied to melanoma, brain and prostatic tumors are also contemplated by the invention as agents that may induce or augment tissue factor expression or release.

The term "radiation" as used herein is defined as the administration of radioactive substances that induce necrosis of tumor tissue, including administration of X-rays or other ionizing radiation.

The term "chemotherapeutic agent" as used herein includes those chemical agents known to produce tumor necrosis and includes such agents as diethylstilbestrol or DES, 5-fluorouracil, methotrexate, interferon-alpha, aspariginase, tamoxifen, flutamide, and others as described in the MERCK MANUAL, 16th edition 1992, (published by Merck Research Laboratories, Rahway, N.J.). In addition, the chemotherapeutic agent can be also be an endotoxin, a cytokine, such as, for example, TNF, or any of the subclasses of cytokines including but not limited to the interleukins, such as, for example, IL-1 and IL-6.

The term "immunotherapeutic agent" or as used herein includes but is not limited to anti-cancer immunotherapeutic agents such as antibodies to tumor antigens, or derived portions of such antibodies. A complete description of the various molecules encompassed in the term antibody is provided below with reference to antibodies that can inhibit TFPI. These same variations apply to antibodies that can act as immunotherapeutic agents according to the method of the invention. The term immunotherapeutic agent also includes any immune-system based therapeutic agent known to act against cancer, including agents that activate T-cells. T-cell activation is known to produce, among other activities, release of interleukins, which, as mentioned above, can cause localized tissue factor release.

The term "inhibitor of TFPI" for use herein, includes but is not limited to any of the below described antagonists of TFPI. The inhibitor of TFPI can be an antibody-based TFPI antagonist, a peptide TFPI antagonist, or a small molecule TFPI antagonist. The use and appropriateness of such inhibitors of TFPI for the purposes of the invention are not limited to any theories of action of the inhibitor. The inhibitor of TFPI, for the purposes of this invention, can be defined as an agent that reduces the biological activity of TFPI in an in vivo or in vitro assay.

The term "cancer" or "tumor" as used herein refers to cancers that do not produce an appreciable amount of tissue factor and those that do. While tissue factor expression and Factor X-activating activity is highly variable among different cancers, some malignancies that are particularly recognized to exhibit either one or both of these TFPI-inhibitable activities, include pancreatic, colon, gastric, breast, lung ovarian, and prostatic adenocarcinomas. The method of treatment of tumors within the scope of the invention therefore may differ for different cancers in different individuals. For example, those cancers that include adenocarcinomas may be responsive to administration of an antagonist of TFPI alone. In contrast, treatment of carcinomas expressing less TF and, therefore, which may be less "procoagulant", may require co-administration of a cytokine, or other TF-inducing/releasing agent in addition to an antagonist of TFPI. Hence, the exact mode of treatment with an inhibitor of TFPI will be determined based in part on the type of cancer being treated.

In one embodiment of the present invention, a TFPI inhibitor is administered to an individual bearing a tumor. The inhibitor of TFPI can be an antibody to TFPI or other antagonist thereto. Antibodies to TFPI can be assayed for effectiveness as antagonists by assaying for reduction of biological activity of TFPI in the presence of the antibodies, polyclonal or monoclonal.

Polyclonal antibodies may be prepared by conventional methods. In general, a solution containing TFPI or an antigenic fragment thereof is first used as an antigen to immunize a suitable animal, such as a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the antigen-containing solution in saline, or preferably in an adjuvant such as Freund's complete adjuvant, and injecting the mixture or emulsion parenterally, generally subcutaneously or intramuscularly. A dose of 50–200 mg/injection is typically sufficient. Immunization is generally boosted 2–6 weeks later with one or more injections of the antigen in saline, preferably using Freund's complete adjuvant. One may alternatively generate antibodies by in vitro immunization using methods known in the art, which for the purposes of this invention is considered equivalent to in vivo immunization.

Polyclonal antibodies are obtained by bleeding the immunized animal into a glass or plastic container, incubating the blood at about 25° C. for about one hour, followed by incubating at about 4° C. for about 2–18 hours. The serum is recovered by centrifugation, for example, 1,000×g for about 10 minutes. About 20–50 ml per bleed may be obtained from rabbits.

Monoclonal antibodies, MAbs, are prepared using the method of Kohler and Milstein, as described in *Nature* (1975) 256: 495–96, or a modification thereof. Typically, a mouse or rat is immunized as described above. However, rather than bleeding the animal to extract serum, the spleen, and optionally several large lymph nodes, is removed and dissociated into single cells. If desired, the spleen cells may be screened, and after removal of nonspecifically adherent cells, applied to a plate or well coated with the protein or polypeptide antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and cultured in a selective medium such as one containing, for example, hypoxanthine, aminopterin, and thymidine (a "HAT" medium). The resulting hybridomas are plated by limiting dilution, and are assayed for the production of antibodies that bind specifically to the immunizing antigen and not to unrelated antigens. The selected MAb-secreting hybridomas are then cultured either in vitro, for example, in tissue culture bottles or hollow fiber reactors, or in vivo, as ascites in mice.

If desired, the antibodies, whether polyclonal or monoclonal, may be labeled using conventional techniques for localization purposes or for assaying purposes. Suitable labels include fluorophores, chromophores, radioactive atoms particularly $^{32}P$ and $^{125}I$, electron-dense reagents, enzymes, and ligands having specific binding partners. Enzymes are typically detected by their activity. For example, horseradish peroxidase (HRP) is usually detected by its ability to convert 3,3',5,5'-tetramethylbenzidine (TMB) to a blue pigment, quantifiable with a spectrophotometer. Specific binding partner refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

The antibodies to TFPI, polyclonal or monoclonal, and preferably monoclonal, for use herein will be compatible to the host to be treated. For example, for treatment of humans, the antibodies can be human monoclonal antibodies or humanized antibodies, as the term is generally known in the art. The humanized antibodies can be made by any number of conventional methods. For example, by cdr (complementarity determining region) grafting, veneering, phage library display, or by use of xeno-mouse. In cdr grafting, the coding regions of the cdr of murine antibodies are linked to the coding regions of the framework regions of human antibodies. In veneering, the canonical regions of the antibodies, including parts of the cdr and parts of the murine framework regions that are exposed on the surface of the molecule, are maintained as well as the murine cdr regions. The antibodies to be administered can be given in a therapeutically effective amount, and can be in the form of a pharmaceutical composition.

In another embodiment of the present invention, the inhibitor of TFPI can be a peptide antagonist. To prepare TFPI peptide antagonists, a peptide library can be screened to determine which peptides function as antagonists. A "library" of peptides may be synthesized and used following the methods disclosed in U.S. Pat. No. 5,010,175, (the '175 patent) and in PCT WO 91/17823. Briefly, one prepares a mixture of peptides, which is then screened to determine the peptides exhibiting the desired TFPI binding or inhibitory activity. In method of the '175 patent, a suitable peptide synthesis support, for example, a resin, is coupled to a mixture of appropriately protected, activated amino acids. The concentration of each amino acid in the reaction mixture is balanced or adjusted in inverse proportion to its coupling reaction rate so that the product is an equimolar mixture of amino acids coupled to the starting resin. The bound amino acids are then deprotected, and reacted with another balanced amino acid mixture to form an equimolar mixture of all possible dipeptides. This process is repeated until a mixture of peptides of the desired length, for example, hexamers, is formed. Note that one need not include all amino acids in each step: one may include only one or two amino acids in some steps, for example, where it is known that a particular amino acid is essential in a given position, thus reducing the complexity of the mixture. After the synthesis of the peptide library is completed, the mixture of peptides is screened for binding to the selected TFPI polypeptide. The peptides are then tested for their ability to inhibit or antagonize TFPI activity. Peptides exhibiting the desired activity are then isolated and sequenced.

The method described in WO 91/17823 is similar. However, instead of reacting the synthesis resin with a mixture of activated amino acids, the resin is divided into twenty equal portions, or into a number of portions corresponding to the number of different amino acids to be added in that step, and each amino acid is coupled individually to its portion of resin. The resin portions are then combined, mixed, and again divided into a number of equal portions for reaction with the second amino acid. In this manner, each reaction may be easily driven to completion. Additionally, one may maintain separate "subpools" by treating portions in parallel, rather than combining all resins at each step. This simplifies the process of determining which peptides are responsible for any observed TFPI antagonism or other activity.

In such cases, the subpools containing, for example, about 1–2,000 candidates each are exposed to the desired TFPI polypeptide. Each subpool that produces a positive result, that is, having binding or inhibitory activity, is then resynthesized as a group of smaller subpools, that is sub-subpools, containing, for example, about 20–100 candidates, and reassayed. Positive sub-subpools may be resynthesized as individual compounds, and assayed finally to determine the peptides that exhibit a high binding constant. These peptides, then, can be tested for their ability to inhibit or antagonize TFPI activity. The methods described in WO 91/17823 and U.S. Pat. No. 5,194,392 enable the preparation of such pools and subpools by automated techniques in parallel, such that all synthesis and resynthesis may be performed in a matter of days.

TFPI peptide antagonists are screened using any available method. The methods described herein are presently preferred. The assay conditions ideally should resemble the conditions under which the TFPI antagonism is exhibited in vivo, that is, under physiologic pH, temperature, ionic strength, etc. Suitable antagonists will exhibit strong inhibition of TFPI activity at concentrations that do not raise toxic side effects in the subject. Antagonists that compete for binding to a TFPI binding site may require concentrations equal to or greater than the competitor concentration, while inhibitors capable of binding irreversibly to TFPI may be added in concentrations on the order of the TFPI concentration.

A further alternative agent that can be used herein as an inhibitor of TFPI is a small molecule antagonist. Small molecules inhibitors can be designed and screened from a pool of synthetic candidates for ability to antagonize TFPI. There exist a wide variety of small molecules, including peptide analogs and derivatives, that can act as inhibitors of proteins and polypeptides. Common practice is to prepare libraries of these types of molecules and screen for those compounds in the libraries that inhibit the activity of the protein of interest, in this case TFPI.

Some general means contemplated for the production of peptides, analogs or derivatives are outlined in CHEMISTRY AND BIOCHEMISTRY OF AMINO ACIDS, PEPTIDES, AND PROTEINS—A SURVEY OF RECENT DEVELOPMENTS, Weinstein, B. ed., Marcell Dekker, Inc., publ. New York (1983). Moreover, substitution of D-amino acids for the normal L-stereoisomer can be carried out to increase the half-life of the molecule.

Peptoids, polymers comprised of monomer units of at least some substituted amino acids, can act as small molecule inhibitors herein and can be synthesized as described in PCT 91/19735, so as to provide libraries of peptoids that can be screened for the desired biological activity. Presently preferred amino acid substitutes are N-alkylated derivatives of glycine, which are easily synthesized and incorporated into polypeptide chains. However, any monomer units which allow for the sequence specific synthesis of pools of diverse molecules are appropriate for use in producing peptoid molecules. The benefits of these molecules for the purpose of the invention is that they occupy different conformational space than a peptide and as such are more resistant to the action of proteases.

Peptoids are easily synthesized by standard chemical methods. The preferred method of synthesis is the "submonomer" technique described by R. Zuckermann et al., *J. Am. Chem. Soc.* (1992) 0114:10646–7. Synthesis by solid phase techniques of heterocyclic organic compounds in which N-substituted glycine monomer units forms a-backbone is described in copending application entitled "Synthesis of N-Substituted Oligomers" filed on Jun. 7, 1995 and is herein incorporated by reference in full. Combinatorial libraries of mixtures of such heterocyclic organic compounds can then be assayed for the ability to inhibit TFPI.

Synthesis by solid phase of other heterocyclic organic compounds in combinatorial libraries is also described in copending application U.S. Ser. No. 08/485,006 entitled "Combinatorial Libraries of Substrate-Bound Cyclic Organic Compounds" filed on Jun. 7, 1995, herein incorporated by reference in full. Highly substituted cyclic structures can be synthesized on a solid support by combining the submonomer method with powerful solution phase chemistry. Cyclic compounds containing one, two, three or more fused rings are formed by the submonomer method by first synthesizing a linear backbone followed by subsequent intramolecular or intermolecular cyclization as described in the application just referenced.

In one embodiment of the present invention, the method of the invention includes systemic or local administration of an inhibitor of TFPI. Where systemic administration is desired, the inhibitor of TFPI may be administered, for example, by intravenous injection or orally. A preferred embodiment of the invention includes local administration of the inhibitor of TFPI, for example, at the tumor site. With local administration of the inhibitor, the preferred mode of administration is by local injection. However, local administration may also be by catheter, or by local deposition, for example by intra- or peritumoral administration of products sold under the trademark DEPOFOAM™ (U.S. Pat. No. 5,442,120, International Publication Nos. WO 95/13796, WO 94/23697 and WO 91/14445, and EP Publication No. 524,968), slow release pump/drug delivery service, implantable or topical gel or polymer, depending on the nature and location of the tumor.

The TFPI inhibitor may be administered alone or, where the nature of the cancer prescribes it, in a preferred embodiment of the invention, the inhibitor may be administered as described earlier, in conjunction with an agent that would induce or augment tissue factor expression or release. If the nature of the cancer being treated does not require the induction of tissue factor because, for example, the tumor itself is constitutively and strongly expressing tissue factor, as with, for example, certain adenocarcinomas, the preferred method of practicing the invention is administration of an inhibitor of TFPI alone. However, where the conditions of the cancer otherwise indicate a need for the simultaneous or prior induction of tissue factor in order to achieve the autoinfarction and subsequent regression of the tumor by the administration of an inhibitor of TFPI, the preferred mode of the invention will include induction or augmentation of tissue factor expression or release by administration of one of the agents previously described for that purpose.

If co-administration of an agent to induce or augment tissue factor expression or release and the TFPI inhibitor is prescribed by the condition of the patient, the inhibitor of TFPI may be co-administered simultaneously or consecutively with the agent that promotes tissue factor expression or release. A preferred embodiment of the invention includes administration of a cytokine that induces or augments tissue factor expression or release, including but not limited to TNF and interleukins. A more preferred embodiment of the invention includes localized co-administration of a cytokine that induces or augments TNF expression or release at the tumor site and co-administration of a small molecule inhibitor of TFPI. A most preferred embodiment of the invention includes subsequent monitoring, by the methods described below, of the tumor for indications of tumor regression, and for purposes of determining subsequent administration protocol for that patient.

Preferred embodiments of the invention include monitoring of the patient after treatment with an inhibitor of TFPI for signs of tumor regression. Such monitoring includes but is not limited to physical exam, CT scan, MRI, mammography, chest X-rays, bone scans, ultra-sounds, bronchoscopy, endoscopy, colonscopy, laparoscopy, and tests for tumor markers such as PSA, CEA, and CA125. The appropriateness of any form of monitoring will be determined by the nature of the cancer being treated.

Administration of the therapeutics of the invention can be accomplished by a gene therapy protocol. In addition, administration of the therapeutics of the invention, including inhibitors of TFPI alone or in conjunction with an administration of an agent that induces release of TF activity can also be accomplished by combining the therapeutic with a pharmaceutically acceptable carrier for administration as, for example, an injectable, oral or other formulation.

The therapeutics of the invention can be administered in a therapeutically effective dosage and amount, in the process of a therapeutically effective protocol for treatment of the patient. The initial and any subsequent dosages administered will depend upon the patient's age, weight, condition, and the disease, disorder or biological condition being treated. Depending on the therapeutic, the dosage and protocol for administration will vary, and the dosage will also depend on the method of administration selected, for example, local or systemic administration.

For polypeptide therapeutics, for example, a polypeptide inhibitor of TFPI or a polypeptide factor that induces the release of TF polypeptide, the dosage can be in the range of about 5 $\mu$g to about 50 $\mu$g/kg of patient body weight, also about 50 $\mu$g to about 5 mg/kg, also about 100 $\mu$g to about 500 $\mu$g/kg of patient body weight, and about 200 to about 250 ug/kg.

For polynucleotide therapeutics, depending on the expression potential of the polynucleotide in the patient, for tissue targeted administration, vectors containing expressable constructs including a coding sequence of an inhibitor of TFPI, or an agent that induces release of TF, or a non-coding sequence that acts as an inhibitor of TFPI or an agent that induces the release of TF, administration is in a range of about 100 ng to about 200 mg of DNA for local administration in a gene therapy protocol, also about 500 ng to about 50 mg, also about 1 ug to about 2 mg of DNA, about 5 ug of DNA to about 500 ug of DNA, and about 20 ug to about 100 ug during a local administration in a gene therapy protocol, and for example, a dosage of about 500 ug, per injection or administration.

Non-coding sequences that act by a catalytic mechanism, for example, catalytically active ribozymes may require lower doses than non-coding sequences that are held to the restrictions of stoichometry, as in the case of, for example, antisense molecules, although expression limitations of the ribozymes may again raise the dosage requirements of ribozymes being expressed in vivo in order that they achieve efficacy in the patient. Factors such as method of action and efficacy of transformation and expression are therefore considerations that will effect the dosage required for ultimate efficacy for DNA and nucleic acids. Where greater expression is desired, over a larger area of tissue, larger amounts of DNA or the same amounts readministered in a successive protocol of administrations, or several administrations to different adjacent or close tissue portions of for example, a tumor site, may be required to effect a positive therapeutic outcome.

For administration of small molecule inhibitors of TFPI, or small molecules that induce the release of TF polypeptide activity, depending on the potency of the small molecule, the dosage may vary. For a very potent inhibitor, microgram ($\mu$) amounts per kilogram of patient may be sufficient, for example, in the range of about 1 $\mu$g/kg to about 500 mg/kg of patient weight, and about 100 $\mu$g/kg to about 5 mg/kg, and about 1 $\mu$g/kg to about 50 $\mu$g/kg, and, for example, about 10 ug/kg. For administration of peptides and peptoids the potency also affects the dosage, and may be in the range of about 1 $\mu$g/kg to about 500 mg/kg of patient weight, and about 100 $\mu$g/kg to about 5 mg/kg, and about 1 $\mu$g/kg to about 50 $\mu$g/kg, and a usual dose might be about 10 ug/kg.

In all cases, routine experimentation in clinical trials will determine specific ranges for optimal therapeutic effect, for each therapeutic, each administrative protocol, and administration to specific patients will also be adjusted to within effective and safe ranges depending on the patient condition and responsiveness to initial administrations.

In preferred embodiments of the invention, administration of the inhibitor of TFPI alone, or the inhibitor of TFPI in conjunction with an agent that induces or augments the expression or release of tissue factor, will be tailored to the individual being treated taking into account such parameters as the type of cancer being treated, and the extent of the disease. A preferred embodiment of the invention includes monitoring the effects of the treatment with an inhibitor of TFPI for signs of tumor regression, and subsequently adjusting the administration of further doses accordingly. For example, a person with breast carcinoma would be treated locally with an agent that induces or augments tissue factor expression or release at the site of the tumor, such as with TNF or Cyclophosphamide methotrexate 5-FU (CMF) or tamoxifen or local radiation therapy. Within the time period of the expression or release of the tissue factor, an inhibitor of TFPI would be co-administered. Such an inhibitor, in a most preferred embodiment of the invention, is a small molecule inhibitor of TFPI. Subsequent mammography, ultrasound, or physical exams, as compared with the same pre-treatment tests, would direct the course and dosage of further treatment. It is contemplated by the invention that more than one dose of an inhibitor of TFPI may be required to bring about the desired regression of the tumor, but it is recognized that such treatment parameters will be tailored to the disease on a patient by patient basis, and ultimately cannot be known until the responsiveness of a given tumor to an initial administration has been determined.

Further objects, features, and advantages of the present invention will become apparent from the following detailed description. It should be understood, however, that the detailed description, while indicating preferred embodiments of the present invention, is given by way of illustration only, since various changes and modifications within the spirit and scope of the invention will become apparent to those skilled in the art from this detailed description.

What is claimed is:

1. A method of inducing or augmenting tissue factor expression or release in a tumorous tissue in an individual comprising administering to the individual a pharmaceutical composition comprising a therapeutically effective amount of an inhibitor of tissue factor pathway inhibitor (TFPI).

2. The method of claim 1, wherein induction or augmentation of tissue factor expression or release is initiated by radiation, cryotherapy, hyperthermia, or by administration of an adjunctive agent.

3. The method of claim 1, wherein the inhibitor of TFPI is an antibody.

4. The method of claim 1, wherein the inhibitor of TFPI is a peptide.

5. The method of claim 1, wherein the inhibitor of TFPI is a peptoid.

6. The method of claim 1, wherein the tumorous tissue is selected from the group consisting of breast cancer, prostate cancer, lung cancer, pancreatic cancer, gastric cancer, colon cancer, ovarian cancer, renal cancer, hepatoma, melanoma, lymphoma, and sarcoma.

7. The method of claim 1, wherein the tumorous tissue is selected from the group consisting of adenocarcinomas including pancreatic, gastric, colon, breast, lung, hepatic, renal, prostatic, or unknown site of origin primary adenocarcinomas.

8. The method of claim 1, wherein the pharmaceutical composition is administered subcutaneously, intravenously, intradermally, orally, or peri- or intra-tumorally.

9. The method of claim 1, wherein the induction or augmentation of tissue factor expression or release occurs by administration of a pharmacological agent effective for induction or augmentation of tissue factor expression or release simultaneously with the administration of the inhibitor of tissue factor pathway inhibitor.

10. The method of claim 1, wherein tissue factor expression or release is induced or augmented by administration of an inhibitor selected from the group consisting of endotoxin, interleukin-1, interleukin-6, and tumor necrosis factor.

11. The method of claim 1, wherein tissue factor expression or release is induced or augmented by administration of a cytokine that is capable of stimulating such expression or release.

12. The method of claim 2, wherein the adjunctive agent is a chemotherapeutic or an immunotherapeutic agent.

13. The method of claim 2, wherein the agent is one selected from the group consisting of endotoxin, interleukin-1, interleukin-6, and tumor necrosis factor.

14. The method of claim 2, wherein the agent is a chemotherapeutic agent selected from the group consisting of DES, 5-fluorouracil, methotrexate, interferon-$\alpha$, aspariginase, tamoxifen, CMF and flutamide.

15. A pharmaceutical composition comprising a therapeutically effective amount of an inhibitor of tissue factor pathway inhibitor (TFPI), a pharmaceutically acceptable carrier, and an adjunctive agent capable of inducing or augmenting expression or release of tissue factor, or an adjunctive agent capable of inducing tissue necrosis.

16. The pharmaceutical composition of claim 15, wherein the adjunctive agent is a chemotherapeutic or immunotherapeutic agent.

17. The pharmaceutical composition of claim 15, wherein the agent is selected from the group consisting of endotoxin, interleukin-1, interleukin-6, and tumor necrosis factor.

* * * * *